(12) United States Patent
Kawaguchi et al.

(10) Patent No.: US 10,166,059 B2
(45) Date of Patent: Jan. 1, 2019

(54) TREATMENT INSTRUMENT

(71) Applicant: OLYMPUS CORPORATION, Hachioji-shi, Tokyo (JP)

(72) Inventors: Yuki Kawaguchi, Koshu (JP); Shinya Masuda, Hino (JP); Tomoyuki Kaga, Hachioji (JP); Hiroto Tomiya, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/730,215

(22) Filed: Oct. 11, 2017

(65) Prior Publication Data

US 2018/0042657 A1 Feb. 15, 2018

Related U.S. Application Data

(63) Continuation of application No. PCT/JP2016/065048, filed on May 20, 2016.

(30) Foreign Application Priority Data

Jul. 16, 2015 (JP) .................................. 2015-142362

(51) Int. Cl.
*A61B 18/18* (2006.01)
*A61B 18/08* (2006.01)
(Continued)

(52) U.S. Cl.
CPC ............ *A61B 18/08* (2013.01); *A61B 18/085* (2013.01); *A61B 18/14* (2013.01);
(Continued)

(58) Field of Classification Search
CPC . A61B 18/08; A61B 18/14; A61B 2018/0089; A61B 2018/00607; A61B 2018/1253; A61B 2018/126
See application file for complete search history.

(56) References Cited

U.S. PATENT DOCUMENTS 4,662,068 A * 5/1987 Polonsky ............... A61B 17/04
30/124
4,985,030 A * 1/1991 Melzer ............... A61B 18/1442
606/51

(Continued)

FOREIGN PATENT DOCUMENTS

JP 2001-61848 A 3/2001
JP 2004-508875 A 3/2004
(Continued)

OTHER PUBLICATIONS

Aug. 23, 2016 Search Report issued in International Patent Application No. PCT/JP2016/065048.
(Continued)

*Primary Examiner* — Michael Peffley
*Assistant Examiner* — Amanda Zink
(74) *Attorney, Agent, or Firm* — Oliff PLC

(57) ABSTRACT

A treatment instrument includes: a first treatment section which includes a first body including a first contact surface and a second body including a second contact surface; a movement mechanism which is configured to switch between a closed position in which the first contact surface and the second contact surface are close to each other, and an opened position in which the first contact surface and the second contact surface are distant from each other; and a second treatment section which is disposed on a distal side along the longitudinal axis with respect to the first treatment section when the first contact surface and the second contact surface are located in the closed position, and which is configured to apply energy to the living tissue to incise or separate the living tissue.

17 Claims, 10 Drawing Sheets

(51) Int. Cl.
  *A61B 18/14* (2006.01)
  *A61B 18/00* (2006.01)
  *A61B 18/12* (2006.01)

(52) U.S. Cl.
  CPC .. *A61B 18/1442* (2013.01); *A61B 2018/0063* (2013.01); *A61B 2018/00083* (2013.01); *A61B 2018/00089* (2013.01); *A61B 2018/00404* (2013.01); *A61B 2018/00607* (2013.01); *A61B 2018/126* (2013.01); *A61B 2018/1253* (2013.01); *A61B 2018/145* (2013.01)

(56) References Cited

U.S. PATENT DOCUMENTS

| | | | | |
|---|---|---|---|---|
| 5,190,541 | A * | 3/1993 | Abele | A61B 18/1442 604/35 |
| 7,582,086 | B2 * | 9/2009 | Privitera | A61B 18/1445 606/205 |
| 8,002,771 | B2 * | 8/2011 | Cox | A61B 17/00234 606/21 |
| 8,083,739 | B2 * | 12/2011 | Messerly | A61B 18/1442 606/205 |
| 9,072,522 | B2 * | 7/2015 | Morejohn | A61B 18/1442 |
| 2006/0217697 | A1 * | 9/2006 | Lau | A61B 17/29 606/29 |

FOREIGN PATENT DOCUMENTS

| | | |
|---|---|---|
| JP | 2005-144192 A | 6/2005 |
| WO | 2014/143472 A1 | 9/2014 |
| WO | 2014/143476 A1 | 9/2014 |

OTHER PUBLICATIONS

Jan. 25, 2018 Translation of International Preliminary Report on Patentability and Written Opinion of International Application No. PCT/JP2016/065048.

Jan. 25, 2018 Translation and Written Opinion of International Application No. PCT/JP2016/065048.

* cited by examiner

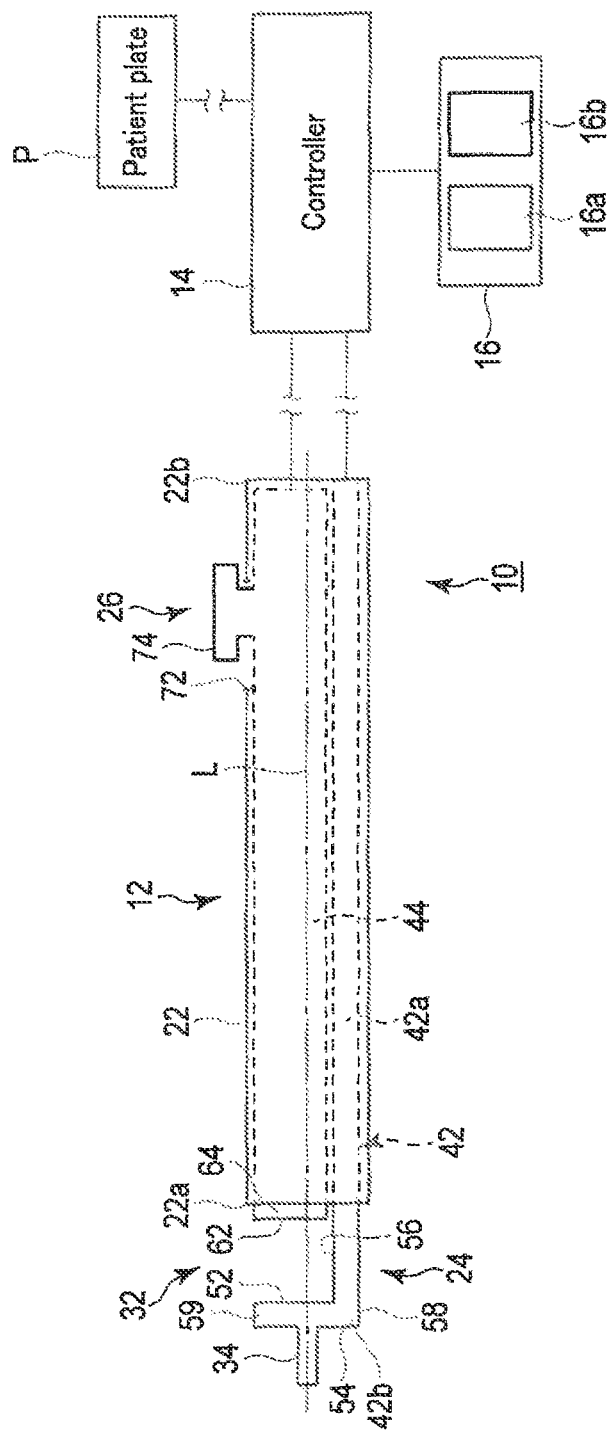
F I G. 1A

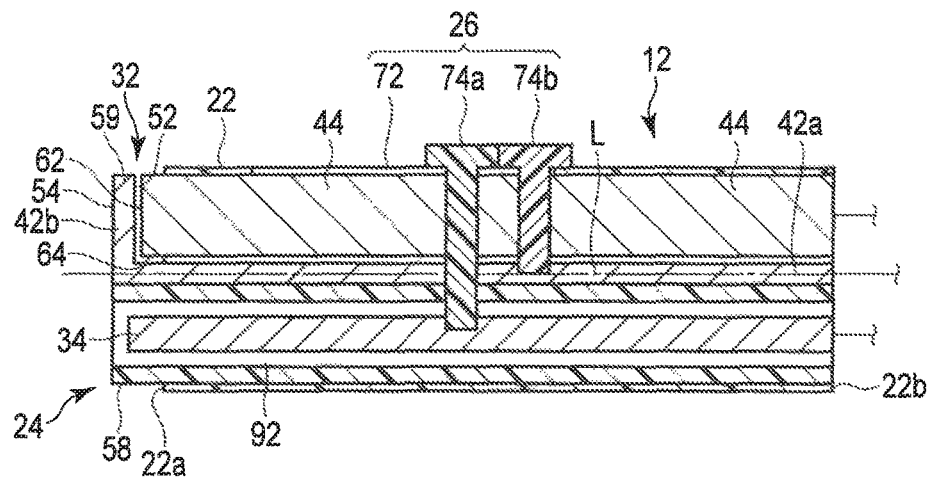
F I G. 11A
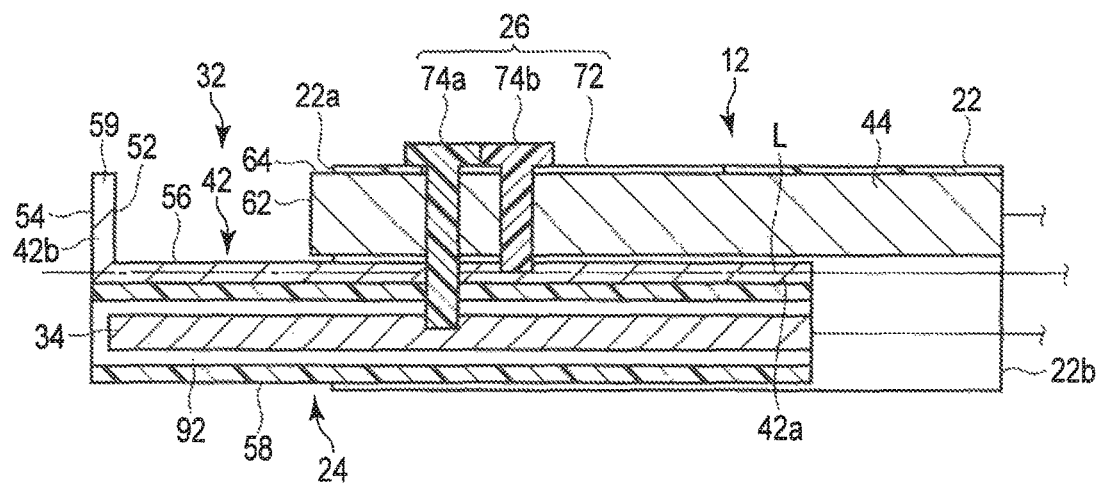
F I G. 11B

TREATMENT INSTRUMENT

CROSS-REFERENCE TO RELATED APPLICATIONS

This application is a Continuation Application of PCT Application No. PCT/JP2016/065048, filed May 20, 2016 and based upon and claiming the benefit of priority from prior Japanese Patent Application No. 2015-142362, filed Jul. 16, 2015, the entire contents of all of which are incorporated herein by reference.

BACKGROUND OF THE INVENTION

1. Field of the Invention

The present invention relates to a treatment instrument.

2. Description of the Related Art

For example, Japanese Patent Application KOKAI Publication No. 2001-61848 discloses a treatment instrument capable of holding a living tissue between a fixed electrode on the distal side and a movable electrode movable to slide along a longitudinal axis direction toward the fixed electrode, to coagulate the living tissue. For example, when a living tissue serving as a treatment target exists in a body cavity or the like, an endoscope and the treatment instrument are put into the body cavity through separate trocars, to perform treatment.

BRIEF SUMMARY OF THE INVENTION

According to an aspect of the invention, there is provided a treatment instrument includes: a sheath which defines a longitudinal axis by a distal end and a proximal end; a first treatment section which includes a first body including a first contact surface configured to contact a living tissue, and a second body including a second contact surface opposed to the first contact surface on a proximal side with respect to the first contact surface and configured to contact the living tissue, and which is configured to apply energy to the living tissue held between the first contact surface and the second contact surface to coagulate the living tissue; a movement mechanism which is configured to move at least one of the first body and the second body along the longitudinal axis, to switch between a closed position in which the first contact surface and the second contact surface are close to each other, and an opened position in which the first contact surface and the second contact surface are distant from each other; and a second treatment section which is disposed on a distal side along the longitudinal axis with respect to the first treatment section when the first contact surface and the second contact surface are located in the closed position, and which is configured to apply energy to the living tissue to incise or separate the living tissue.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1A is a schematic diagram illustrating a treatment system according to a first embodiment, and illustrating a state in which a first treatment section of a treatment area of a treatment instrument is switched to an opened position;

FIG. 11A is a schematic diagram illustrating a state in which a movement mechanism of a treatment instrument of a treatment system according to a seventh embodiment is operated to switch a first treatment section of a treatment area is switched to a closed position, and a second treatment section is retracted into the first treatment section;

FIG. 11B is a schematic diagram illustrating a state in which the movement mechanism of the treatment instrument of the treatment system according to the seventh embodiment is operated to switch the first treatment section of the treatment area is switched to an opened position, and the second treatment section is retracted into the first treatment section.

DESCRIPTION OF EMBODIMENTS

Embodiments will be explained hereinafter with reference to drawings.

A first embodiment will be explained with reference to FIG. 1A to FIG. 2.

As illustrated in FIG. 1A, a treatment system (treatment instrument unit) 10 according to the present embodiment includes a treatment instrument 12, and a controller 14. A foot switch 16 is connected with the controller 14. The treatment instrument 12 may be provided with a hand switch (not illustrated), together with the foot switch 16, or instead of the foot switch 16. A patient plate P is connected with the controller 14.

Figure 1B:
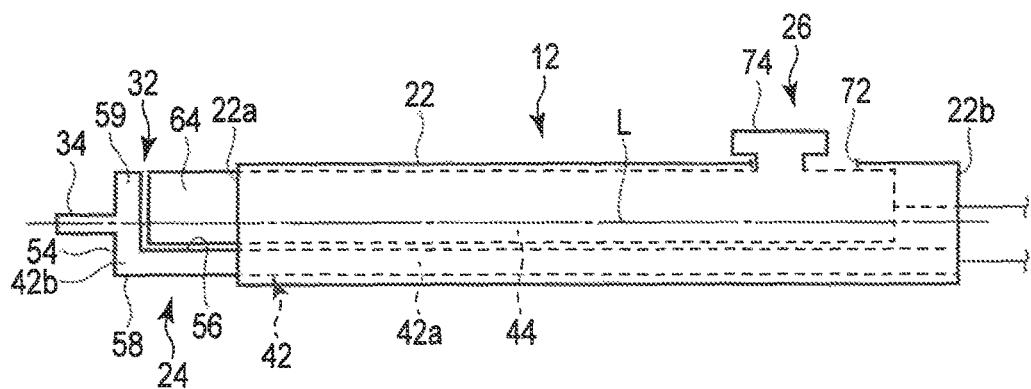
FIG. 1B is a schematic diagram illustrating the treatment instrument of the treatment system according to the first embodiment, and illustrating a state in which the first treatment section of the treatment area is switched to a closed position.
Figure 2:
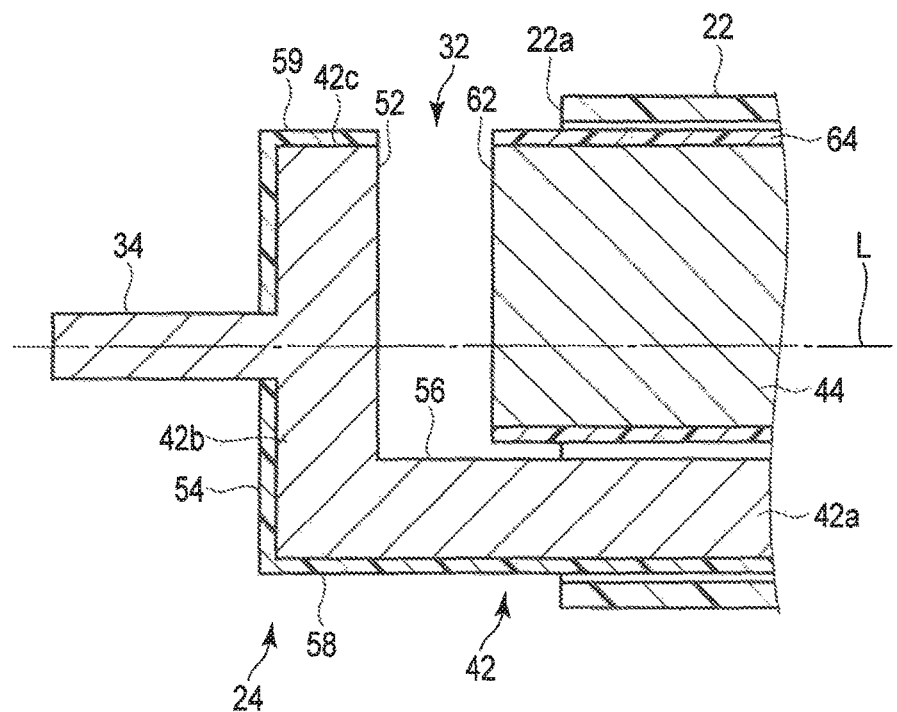
FIG. 2 is a schematic vertical cross-sectional view illustrating the treatment area of the treatment instrument illustrated in FIG. 1A in an enlarged state.

As illustrated in FIG. 1A and FIG. 1B, the treatment instrument 12 includes a cylindrical sheath 22, a treatment area 24 projecting from a distal end 22a of the sheath 22, and a movement mechanism 26. The sheath 22 defines a longitudinal axis L with its distal end 22a and proximal end 22b. The sheath 22 has electrical insulation property. The treatment area 24 includes a first treatment section 32 and a second treatment section 34. In FIG. 1A to FIG. 2, the second treatment section 34 has a straight shape, but the shape of the second treatment section 34 is not particularly limited. The second treatment section 34 may have a proper shape, such as a hook shape and a spatula shape, to be used.

In the present embodiment, the first treatment section 32 is capable of performing bipolar-type treatment. The first treatment section 32 includes a first body 42 and a second body 44. Each of the first body 42 and the second body 44 is preferably formed of a metal material having conductivity. The first body 42 and the second body 44 may be formed of the same material, or different materials. The first body 42 and the second body 44 are electrically connected with the controller 14.

In the present embodiment, the first body 42 includes a shaft 42a extending, for example, in parallel with the longitudinal axis L, and an action section 42b formed by bending a distal end of the shaft 42a in a direction crossing the longitudinal axis L. The action section 42b is bent, for example, in a substantial L shape. In FIG. 1A to FIG. 2, the angle of the action section 42b with respect to the shaft 42a is illustrated as 90°, but the angle is not limited to 90°. The action section 42b may be bent at a proper angle. A portion between the sections denoted by reference numerals 54 and 58 described later, that is, a boundary portion between the shaft 42a and the action section 42b is preferably formed as a curved surface, such as a chamfered surface, as a matter of course. The second body 44 is extended, for example, in parallel with the longitudinal axis L, in the same manner as the shaft 42a of the first body 42, and formed as, for example, a column-like rod.

The action section 42b of the first body 42 includes a first contact surface 52 treating the living tissue in a state of contacting the living tissue. The action section 42b of the first body 42 projects from the distal end 22a of the sheath 22. The first contact surface 52 is opposed to the distal end 22a of the sheath 22. Specifically, the first contact surface 52 is opposed to the proximal side along the longitudinal axis L.

The second body 44 includes a second contact surface 62 disposed on the proximal side along the longitudinal axis L with respect to the first contact surface 52, opposed to the first contact surface 52, and treating the living tissue in a state of contacting the living tissue together with the first contact surface 52. The second contact surface 62 is opposed to the distal side along the longitudinal axis L. The first contact surface 52 and the second contact surface 62 are preferably parallel with each other.

In the present embodiment, each of the first contact surface 52 and the second contact surface 62 is used as a high-frequency electrode. In addition, the first contact surface 52 and the second contact surface 62 of the first treatment section 32 is capable of performing bipolar-type treatment to enable coagulation, such as sealing, of the held living tissue, when energy is provided in a state in which the living tissue is held between the first contact surface 52 and the second contact surface 62. When the living tissue is a blood vessel, the held blood vessel is sealed by bipolar-type treatment.

The first body 42 includes an electrical insulation section 54 to prevent treatment of the living tissue, when the energy described above is provided in a state of contacting the living tissue. The electrical insulation section 54 is formed of, for example, insulation coating. The electrical insulation section 54 preferably has heat resistance. The electrical insulation section 54 is formed on a back surface with respect to the first contact surface 52. Specifically, the electrical insulation section 54 is disposed on the distal end surface of the first body 42, and opposed to the distal side along the longitudinal axis L.

In the shaft 42a of the first body 42, a portion denoted by reference numeral 56 disposed in the vicinity of the boundary with the action section 42b and close to the distal end of the second body 44 may be formed as an electrode, in the same manner as the first contact surface 52, or may be formed as an electrical insulation section. An electrical insulation section 58 is formed on a back surface (far surface) of the portion denoted by reference numeral 56. The electrical insulation sections 54 and 58 are preferably continuously formed in seamless manners. The electrical insulation section 58 is formed of, for example, insulation coating. The first body 42 prevents treatment of the living tissue, not only with the electrical insulation section 54 but also the electrical insulation section 58, when the energy described above is provided in a state of contacting the living tissue.

The side surface between the first contact surface 52 and the electrical insulation section 54, the side surface between the portion denoted by reference numeral 56 and the electrical insulation section 58, and a far end 42*c* of the action section 42*b* of the first body 42 with respect to the shaft 42*a* that is long along the longitudinal axis L are preferably formed as an electrical insulation section 59. The far end 42*c* formed an opening inlet through which the living tissue is disposed between the second contact surface 62 of the second body 44 and the opening inlet.

The second body 44 includes an electrical insulation section 64 preventing treatment of the living tissue when the energy described above is provided in a state of contacting the living tissue. The electrical insulation section 64 is formed in a portion excluding the second contact surface 62.

Specifically, an external circumferential surface around the longitudinal axis of the second body 44 is provided with insulation coating. With the insulation coating, a sliding surface between the first body 42 and the second body 44 is electrically insulated. The electrical insulation section 64 preferably has heat resistance.

The first body 42 illustrated in FIG. 1A and FIG. 1B is fixed with respect to the sheath 22, and the second body 44 is movable with respect to the sheath 22 along the longitudinal axis L. The movement mechanism 26 is capable of moving the second body 44 within a predetermined range along the longitudinal axis L. A proper mechanism may be used as the movement mechanism 26. For example, a linear motor may be used to move the second body 44 within a predetermined range along the longitudinal axis L with respect to the sheath 22. This explanation illustrates an example of the movement mechanism 26, in which the user manually moves the second body 44 with respect to the sheath 22 along the longitudinal axis L.

The sheath 22 is provided with a groove 72. The groove 72 is longer along the longitudinal axis L than in a circumferential direction of the longitudinal axis L, and defines the movement range in which the second body 44 is moved along the longitudinal axis L. The groove 72 is provided with a slide lever 74 as an operation body. The slide lever 74 is movable between a distal end and a proximal end of the groove 72 along the longitudinal axis L. The slide lever 74 has electrical insulation property. The slide lever 74 is coupled with the second body 44. Specifically, as an example, the movement mechanism 26 includes the groove 72 formed in the sheath 22, and the slide lever 74 coupled with the second body 44. FIG. 1A and FIG. 1B illustrate that the groove 72 and the slide lever 74 are located in a position close to the proximal end 22*b* in the sheath 22, but the groove 72 and the slide lever 74 may be located in a position close to the distal end 22*a*, as a matter of course.

The movement mechanism 26 is capable of causing the slide lever 74 to abut against the distal end of the groove 72, when the slide lever 74 is moved along the longitudinal axis L toward the distal side of the sheath 22. In addition, the movement mechanism 26 is capable of causing the slide lever 74 to abut against the proximal end of the groove 72, when the slide lever 74 is moved along the longitudinal axis L toward the proximal side of the sheath 22. As described above, the groove 72 can define the movable range of the slide lever 74.

When the slide lever 74 is caused to abut against the distal end of the groove 72 of the sheath 22 along the longitudinal axis L, the second contact surface 62 of the second body 44 is moved toward the distal side along the longitudinal axis L and close to the first contact surface 52 of the first body 42. For this reason, the first treatment section is changed to a closed position in which the first contact surface 52 of the first body 42 and the second contact surface 62 of the second body 44 are close to each other. In this state, the first contact surface 52 and the second contact surface 62 do not contact each other, but a small space is formed therebetween. When the slide lever 74 is caused to abut against the proximal end of the groove 72 of the sheath 22 along the longitudinal axis L, the second contact surface 62 of the second body 44 is moved toward the proximal side along the longitudinal axis L and distant from the first contact surface 52 of the first body 42. For this reason, the first treatment section is changed to an opened position in which the first contact surface 52 of the first body 42 and the second contact surface 62 of the second body 44 are distant from each other. Operating the slide lever 74 enables adjustment of a distance between the first contact surface 52 and the second contact surface 62, and adjustment of the opening quantity. Specifically, the movement mechanism 26 is capable of moving the second body 44 along the longitudinal axis L, to switch between the closed position in which the first contact surface 52 and the second contact surface 62 are close to each other, and the opened position in which the first contact surface 52 and the second contact surface 62 are distant from each other.

The second treatment section 34 is disposed on the distal side with respect to the first treatment section 32 along the longitudinal axis L. In this example, the second treatment section 34 is formed as one unitary piece with the first body 42. In this case, the second treatment section 34 has the same potential as that of the first body 42.

The second treatment section 34 projects toward the distal side along the longitudinal axis L with respect to the electrical insulation section 54 on the distal end surface of the first body 42. The second treatment section 34 is formed in a rod shape thinner than the second body 44. FIG. 1A to FIG. 2 illustrate that the second treatment section 34 has a shape extending in a straight manner along the longitudinal axis L, but the shape may be properly set as described above. The second treatment section 34 is used as a high-frequency electrode. The second treatment section 34 is capable of performing monopolar-type treatment to incise and exfoliate the contacting living tissue, when energy is provided in a state of contacting the living tissue between the second treatment section 34 and the patient plate P attached to the patient. Specifically, the second treatment section 34 is disposed on the distal side with respect to the first treatment section 32 along the longitudinal axis L when the first contact surface 52 and the second contact surface 62 are located in the closed position, and capable of incising or exfoliating the living tissue by applying energy to the living tissue.

In the present embodiment, the controller 14 is capable of performing control to output energy to the first treatment section 32 and perform bipolar-type treatment with the first treatment section 32, in accordance with an instruction with the foot switch 16, for example, and capable of performing control to output energy to the second treatment section 34 and perform monopolar-type treatment with the second treatment section 34. In the present embodiment, the first body 42 is used when either of the treatments is performed.

The foot switch 16 of the treatment system 10 according to the present embodiment includes a first switch 16*a* and a second switch 16*b*. By a pressing operation, the first switch 16*a* outputs signal to the controller 14 to output energy from the controller 14, when bipolar-type treatment is performed with the first treatment section 32. By a pressing operation, the second switch 16b outputs signal to the controller 14 to output energy from the controller 14, when monopolar-type treatment is performed with the second treatment section 34.

The following is brief explanation of functions of the treatment system 10 according to the present embodiment. As an example, the treatment instrument 12 is used together with an endoscope (not illustrated), through a trocar.

The user attaches the patient plate P to a proper position of the patient. The user properly holds the treatment instrument 12, and causes the treatment area 24 to face a membrane tissue or a layered tissue in the body, while checking the observed image of the endoscope. Since the second treatment section 34 of the treatment area 24 is formed thin, its approaching property is maintained.

The second switch 16b is pressed, to perform monopolar-type treatment on the living tissue with the second treatment section 34 of the treatment area 24. The monopolar-type high-frequency energy is applied to the living tissue serving as treatment target, and the high-frequency current is recovered with the patient plate P attached to the patient, to incise the living tissue contacting the second treatment section 34, or separate the layers. The operation of pressing the second switch 16b is performed only when treatment such as incision is to be actually performed, and usually pressing of the second switch 16b is released.

When the electrical insulation sections 54, 58, and 59 of the first treatment section 32 contact the living tissue in a proper position, no current flows through the contacting living tissue. With the structure, the electrical insulation sections 54, 58, and 59 of the first treatment section 32 prevent a high-frequency current from flowing through the living tissue unintentionally. Specifically, this structure prevents the treatment area 24 from performing unintentional treatment.

A blood vessel may be exposed, in the case of repeating treatment to incise a living tissue in a thin-membrane shape or separate the layers of the living tissue. In such a case, the blood vessel is sealed, that is, coagulated, to prevent bleeding from the blood vessel.

Specifically, the user operates the slide lever 74 along the groove 72, to switch the first contact surface 52 of the first body 42 and the second contact surface 62 of the second body 44 to the opened position. In this state, the blood vessel is disposed between the first contact surface 52 of the first body 42 and the second contact surface 62 of the second body 44 in the first treatment section 32. The user moves the slide lever 74 to switch the first contact surface 52 of the first body 42 and the second contact surface 62 of the second body 44 to the closed position. In this state, the blood vessel contacts both the first contact surface 52 of the first body 42 and the second contact surface 62 of the second body 44. The first contact surface 52 and the second contact surface 62 are not electrically connected. In this state, the first switch 16a is pressed, to perform bipolar-type treatment on the living tissue serving as treatment target, such as a blood vessel, with the first treatment section 32. High-frequency energy is applied to the blood vessel (living tissue) serving as treatment target, to coagulate the blood vessel contacting both the first contact surface 52 of the first body 42 and the second contact surface 62 of the second body 44 in the first treatment section 32, by Joule heat. This operation prevents bleeding from the coagulated region. When a blood vessel is cut, the second treatment section 34 is used to cut the coagulated region. This operation can be performed only by moving the treatment area 24, and does not require change of the treatment instrument 12 itself.

When the first treatment section 32 is switched from the opened position to the closed position, or from the closed position to the opened position, the first and the second bodies 42 and 44 are only moved relatively in the front and the rear direction. This structure is simple, and hardly hampers visibility when a blood vessel or the like is disposed between the first contact surface 52 of the first body 42 and the second contact surface 62 of the second body 44.

Thereafter, while monopolar-type treatment is performed, such as incision with the second treatment section 34, bipolar-type treatment is performed with the first treatment section 32 when a blood vessel or the like is exposed. If necessary, monopolar-type treatment is performed with the second treatment section 34, to cut the blood vessel sealed by the bipolar-type treatment, and desired treatment is ended.

As explained above, the following can be said with the treatment instrument 12 according to the present embodiment.

In a state in which the treatment area 24 is brought close to the living tissue serving as treatment target, incision or separation can be performed on the living tissue serving as treatment target. In addition, even when a blood vessel is exposed in the state, the blood vessel can be sealed, while the state in which the treatment area 24 is brought close to the living tissue is maintained. Accordingly, treatment on the living tissue serving as treatment target can be performed with one treatment instrument 12, without changing the treatment instrument. This structure enables reduction in treatment time, and greatly improves treatment property for the living tissue serving as treatment target.

For example, when the treatment instrument 12 is used together with an endoscope, it is unnecessary to change the treatment instrument 12 for another treatment instrument. This structure maintains the state in which the treatment area 24 is always disposed close to the treatment target, while the treatment area 24 is disposed within the observation visual field of the endoscope. This structure removes the labor of disposing the treatment area 24 in the visual field of the endoscope, when once the treatment area 24 is disposed in the visual field of the endoscope. Specifically, treatment can be performed in the state where the treatment area 24 is disposed in the visual field of the endoscope, only by once causing the treatment area 24 to face the living tissue serving as treatment target.

Figure 3A:
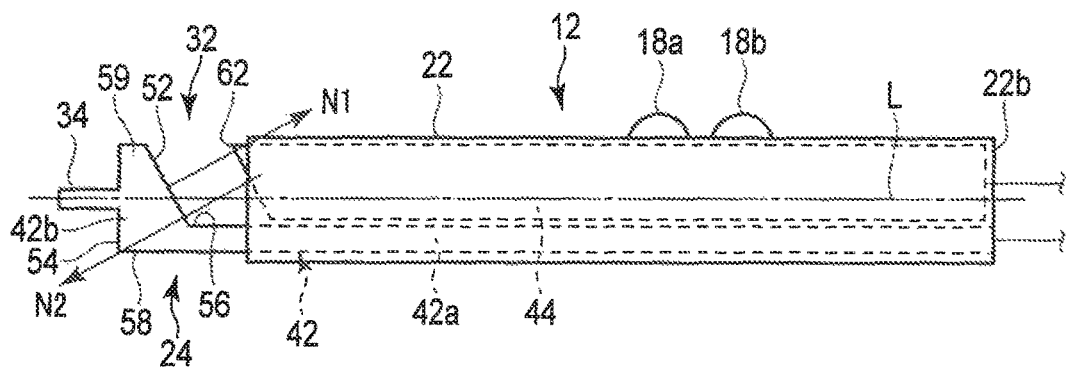
FIG. 3A is a schematic diagram illustrating a treatment instrument of a treatment system according to a second embodiment, and illustrating a state in which a first treatment section of a treatment area is switched to an opened position.
Figure 3B:
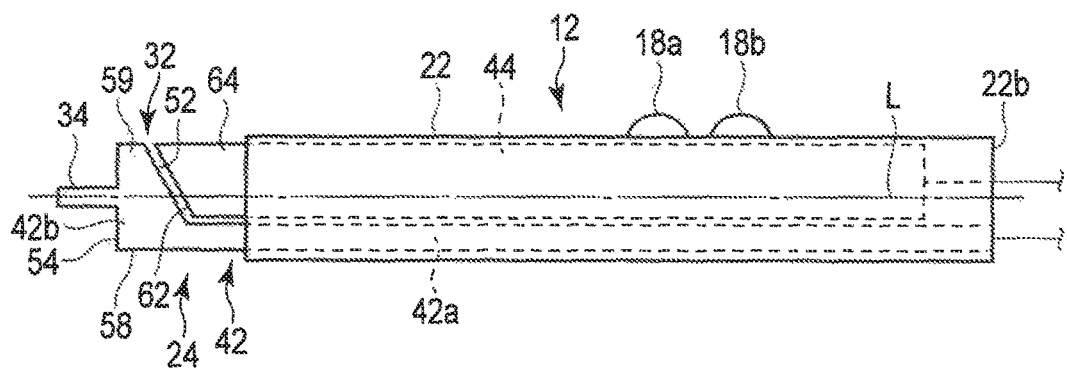
FIG. 3B is a schematic diagram illustrating the treatment instrument of the treatment system according to the second embodiment, and illustrating a state in which the first treatment section of the treatment area is switched to a closed position.

The following is explanation of a second embodiment, with reference to FIG. 3A and FIG. 3B. The present embodiment is a modification of the first embodiment. The same members or members having the same functions as the members explained in the first embodiment are denoted by the same reference numerals as much as possible, and detailed explanation thereof is omitted.

As illustrated in FIG. 3A and FIG. 3B, each of the first contact surface 52 of the first body 42 and the second contact surface 62 of the second body 44 is formed as an inclined surface inclined with respect to a state of being orthogonal to the longitudinal axis L. A normal N1 of the first contact surface 52 of the first body 42 is directed toward the proximal side along the longitudinal axis L, and toward the upper side in FIG. 3A opposite to the shaft 42a of the first body 42. Since the first contact surface 52 of the first body 42 is formed as an inclined surface, for example, when the treatment area 24 is moved toward the distal side along the longitudinal axis L, the first contact surface 52 is capable of easily guiding, for example, a blood vessel, between the first body 42 and the second body 44.

In this example, a normal N2 of the second contact surface 62 of the second body 44 is directed toward the distal side along the longitudinal axis L, and toward the lower side in FIG. 3A and in the vicinity of the boundary between the shaft 42a and the action section 42b of the first body 42. The normals N1 and N2 are preferably parallel with each other. Specifically, the first contact surface 52 and the second contact surface 62 are preferably parallel with each other. The first contact surface 52 of the first body 42 and the second contact surface 62 of the second body 44 secure larger contact areas for the living tissue, such as a blood vessel, than those of the first contact surface 52 of the first body 42 and the second contact surface 62 of the second body 44 explained in the first embodiment. This structure easily increases the contact area when, for example, a thicker blood vessel is brought into contact with the first contact surface 52 of the first body 42 and the second contact surface 62 of the second body 44. This structure also enables treatment, such as sealing the living tissue with a substantially uniform thickness, when the living tissue such as a blood vessel is disposed between the first contact surface 52 of the first body 42 and the second contact surface 62 of the second body 44.

In this example, a first switch 18a and a second switch 18b are provided on the external circumferential surface of the sheath 22. In accordance with an instruction by an operation of pressing the first switch 18a, the controller 14 issues an instruction to output energy from the controller 14, when bipolar-type treatment is performed with the first treatment section 32. In accordance with an instruction by an operation of pressing the second switch 18b, the controller 14 also issues an instruction to output energy from the controller 14, when monopolar-type treatment is performed with the second treatment section 34. Output of energy from the controller 14 can be controlled also by operation of the foot switch 16, as well as the switches 18a and 18b on the external circumferential surface of the sheath, as a matter of course.

The treatment instrument 12 according to the present embodiment can be used in the same manner as the treatment instrument 12 explained in the first embodiment, and explanation of the functions thereof is omitted.

With the treatment instrument 12 according to the present embodiment, because the first contact surface 52 and the second contact surface 62 are formed as inclined surfaces, the contact areas are increased when a blood vessel or the like is held with the first treatment section 32. Accordingly, this structure enables securer sealing treatment even on a relatively thick blood vessel.

Figure 4:
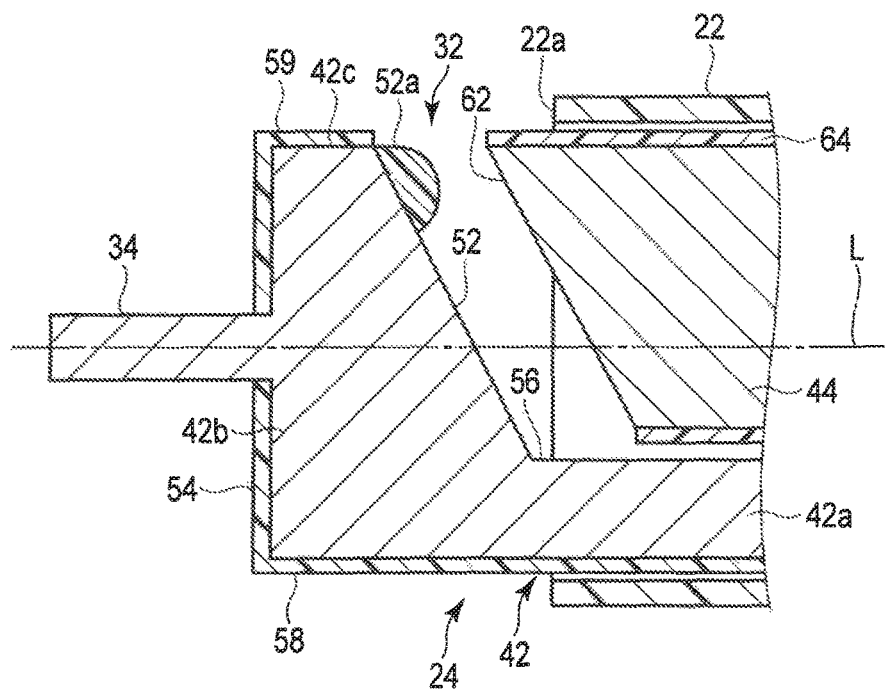
FIG. 4 is a schematic vertical cross-sectional view illustrating the treatment area of the treatment instrument illustrated in FIG. 3A in an enlarged state.

The following is explanation of a modification of the second embodiment, with reference to FIG. 4.

As illustrated in FIG. 4, a projection 52a having electrical insulation property is disposed on the first contact surface 52 of the first body 42. The projection 52a is preferably disposed in the vicinity of the far end 42c with respect to the shaft 42a that is long along the longitudinal axis L, in the action section 42b of the first body 42. Existence of the projection 52a also allows a blood vessel to enter a space between the first contact surface 52 of the first body 42 and the second contact surface 62 of the second body 44, when the first body 42 and the second body 44 are located in the opened position. By contrast, when the first body 42 and the second body 44 are located in the closed position, the projection 52a suppresses the blood vessel from unintentionally escaping from the space between the first contact surface 52 of the first body 42 and the second contact surface 62 of the second body 44. The projection 52a can also be used as a spacer maintaining a distance between the first contact surface 52 and the second contact surface 62.

Figure 5A:
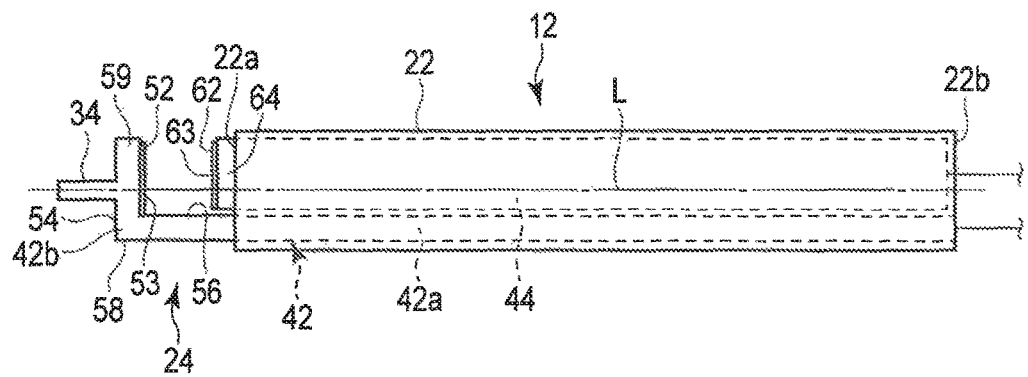
FIG. 5A is a schematic diagram illustrating a treatment instrument of a treatment system according to a third embodiment, and illustrating a state in which a first treatment section of a treatment area is switched to an opened position.
Figure 5B:
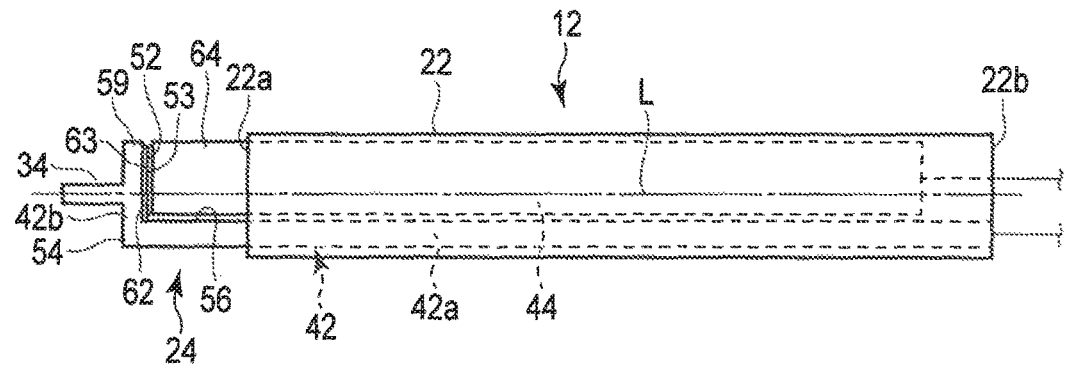
FIG. 5B is a schematic diagram illustrating the treatment instrument of the treatment system according to the third embodiment, and illustrating a state in which the first treatment section of the treatment area is switched to a closed position.
Figure 6:
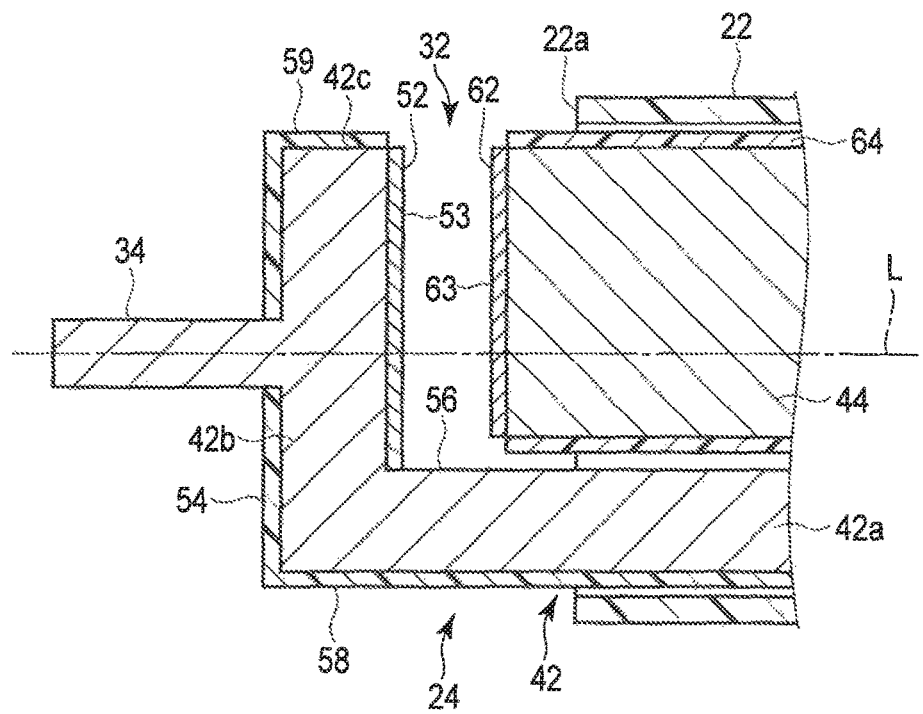
FIG. 6 is a schematic vertical cross-sectional view illustrating the treatment area of the treatment instrument illustrated in FIG. 5A in an enlarged state.

The following is explanation of a third embodiment with reference to FIG. 5A to FIG. 6. The present embodiment is a modification of the first embodiment and the second embodiment. The same members or members having the same functions as the members explained in the first and the second embodiments are denoted by the same reference numerals as much as possible, and detailed explanation thereof is omitted.

As illustrated in FIG. 5A to FIG. 6, the first contact surface 52 of the first body 42 includes a first heater 53, instead of being used as a high-frequency electrode. The second contact surface 62 of the second body 44 includes a second heater 63, instead of being used as a high-frequency electrode. When neither the first contact surface 52 nor the second contact surface 62 is used as a high-frequency electrode like this, the first heater 53 and the second heater 63, that is, the first contact surface 52 and the second contact surface 62 may contact each other, as illustrated in FIG. 5B. Each of the first heater 53 and the second heater 63 is preferably formed in a plate shape enabling increase in temperature to approximately several hundred degrees C. for several seconds.

The treatment instrument 12 according to the present embodiment can be used in the same manner as the treatment instrument 12 explained in the first embodiment, and explanation of the functions thereof is omitted. With the first heater 53 and the second heater 63, this structure enables coagulation of the living tissue with the first treatment section 32, and treatment to seal the living tissue when the living tissue is a blood vessel. With the first heater 53 and the second heater 63, this structure enables incision of the living tissue, as well as coagulation of the living tissue, by setting the energy quantity.

The treatment instrument 12 according to the present embodiment enables treatment, such as coagulation of the living tissue, with the first treatment section 32 without using a high-frequency current. Specifically, the energy used for treatment with the treatment instrument 12 is not limited to high-frequency energy, but thermal energy may be properly used.

It suffices that the treatment instrument 12 includes at least one of the first heater 53 and the second heater 63. Specifically, this explanation illustrates the case of including both the first heater 53 and the second heater 63, but the treatment instrument 12 may include only one of them.

For example, when energy is applied to the first heater 53 to cause the first heater 53 to generate heat, the heat enables sealing of the living tissue such as a blood vessel in the first treatment section 32, and enables transmission of heat to the second treatment section 34 through the action section 42b of the first body 42. The first heater 53 set to a certain temperature enables incision of the tissue in a coagulated state, such as a blood vessel, as well as coagulation of the living tissue. In addition, the first heater 53 set to a certain temperature enables incision of the living tissue with the heat from the first heater 53, without providing energy to the second treatment section 34, immediately after the blood vessel is sealed.

As described above, the present embodiment is a modification of the second embodiment. For this reason, in the FIG. 5A to FIG. 6, the first contact surface 52 and the second contact surface 62, that is, the first heater 53 and the second heater 63 may be formed as inclined surfaces illustrated in FIG. 3A to FIG. 4, as a matter of course.

The first contact surface 52 of the first treatment section 32 may be formed as an electrode, and the first heater 53 may be embedded in the first contact surface 52. The second contact surface 62 of the first treatment section 32 may be formed as an electrode, and the second heater 63 may be embedded in the second contact surface 62. Specifically, each of the first contact surface 52 and the second contact surface 62 of the first treatment section 32 is used as a high-frequency electrode and as a heater. In such a case, as explained in the first and the second embodiments, the first contact surface 52 and the second contact surface 62 do not contact each other. The first contact surface 52 and the second contact surface 62 are capable of coagulating and incising the living tissue with the thermal energy from the heaters 53 and 63, respectively, while sealing the living tissue such as a blood vessel with high-frequency energy. For example, a relatively thick blood vessel may require a long time for sealing the blood vessel with high-frequency energy, but the treatment ability can be increased by using the high-frequency energy together with the thermal energy from the heater 53, to shorten the time required for sealing the blood vessel.

Figure 7A:
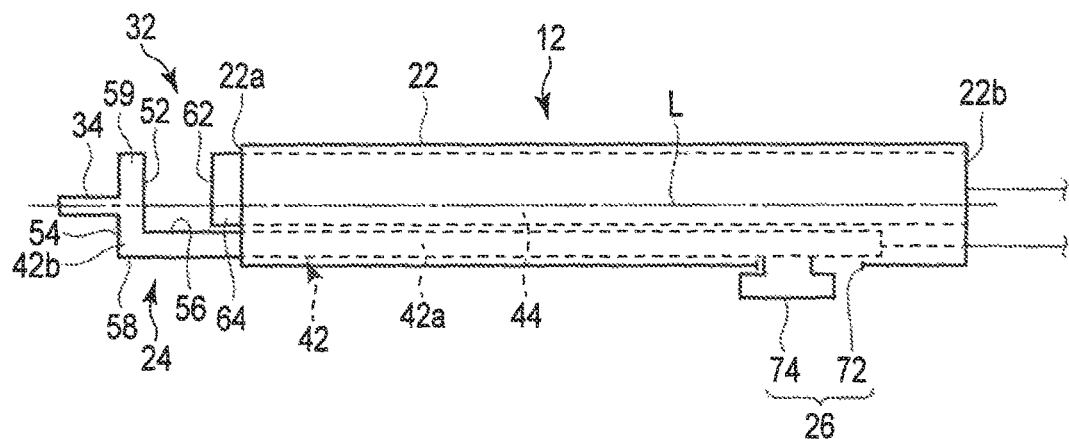
FIG. 7A is a schematic diagram illustrating a treatment instrument of a treatment system according to a fourth embodiment, and illustrating a state in which a first treatment section of a treatment area is switched to an opened position.
Figure 7B:
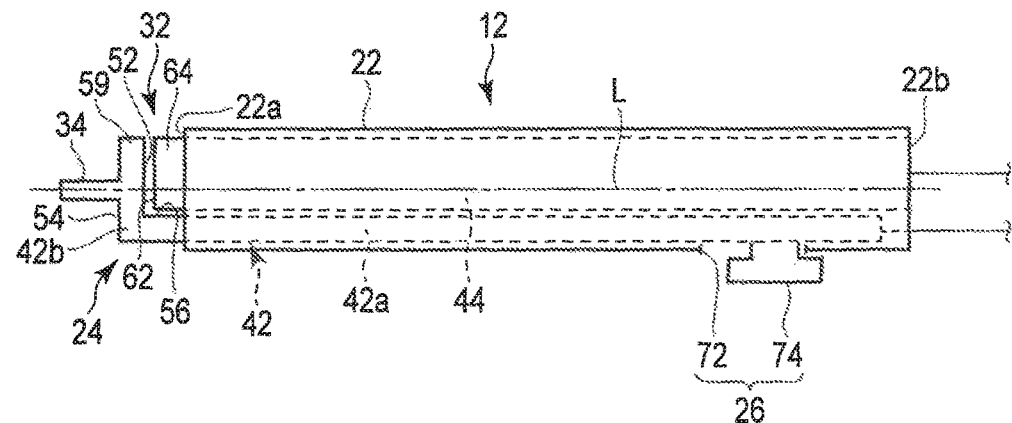
FIG. 7B is a schematic diagram illustrating the treatment instrument of the treatment system according to the fourth embodiment, and illustrating a state in which the first treatment section of the treatment area is switched to a closed position.

The following is explanation of a fourth embodiment, with reference to FIG. 7A and FIG. 7B. The present embodiment is a modification of the first to the third embodiments. The same members or members having the same functions as the members explained in the first to the third embodiments are denoted by the same reference numerals as much as possible, and detailed explanation thereof is omitted.

As illustrated in FIG. 1A and FIG. 1B, in the first embodiment, the first body 42 of the first treatment section 32 is fixed with respect to the sheath 22, and the second body 44 is movable with respect to the first body 42 and the sheath 22. As illustrated in FIG. 7A and FIG. 7B, the present embodiment has a structure in which the second body 44 of the first treatment section 32 is fixed with respect to the sheath 22, and the first body 42 is movable with respect to the second body 44 and the sheath 22. Specifically, the movement mechanism 26 is capable of moving the first body 42 within a predetermined range along the longitudinal axis L. As explained in the first embodiment, a proper mechanism may be used as the movement mechanism 26. For example, a linear motor may be used to move the first body 42 within a predetermined range along the longitudinal axis L with respect to the sheath 22. This explanation illustrates an example of the movement mechanism 26, in which the user manually moves the first body 42 with respect to the sheath 22 along the longitudinal axis L.

The groove 72 formed in the sheath 22 is provided with a slide lever 74 as an operation body. The slide lever 74 has electrical insulation property. The slide lever 74 is coupled with the first body 42. Specifically, as an example, the movement mechanism 26 includes the groove 72 formed in the sheath 22, and the slide lever 74 coupled with the first body 42.

The movement mechanism 26 is capable of defining the movable range of the slide lever 74 by the groove 72. When the slide lever 74 is caused to contact the distal end of the groove 72 of the sheath 22 along the longitudinal axis L, the first contact surface 52 of the first body 42 is moved toward the distal side along the longitudinal axis L and distant from the second contact surface 62 of the second body 44. For this reason, the first contact surface 52 of the first body 42 and the second contact surface 62 of the second body 44 are distant from each other, and in the opened position. When the slide lever 74 is caused to contact against the proximal end of the groove 72 of the sheath 22 along the longitudinal axis L, the first contact surface 52 of the first body 42 is moved toward the proximal side along the longitudinal axis L and close to the second contact surface 62 of the second body 44. For this reason, the first contact surface 52 of the first body 42 and the second contact surface 62 of the second body 44 are close to each other and in the closed position. Specifically, the movement mechanism 26 is capable of moving the first body 42 along the longitudinal axis L, to switch between the closed position in which the first contact surface 52 and the second contact surface 62 are close to each other, and the opened position in which the first contact surface 52 and the second contact surface 62 are distant from each other. In the closed position, the first contact surface 52 and the second contact surface 62 do not contact each other, but a small gap is formed therebetween.

Other structures of the treatment instrument 12 are the same as those of the first embodiment, and explanation is omitted herein. The treatment instrument 12 according to the present embodiment can be used in the same manner as the treatment instrument 12 explained in the first embodiment, and explanation of functions thereof is omitted.

The treatment instrument 12 according to the present embodiment can be used in the same manner as explained in the first embodiment, even when the first body 42 is formed movable with respect to the sheath 22 and the second body 44.

Figure 8A:
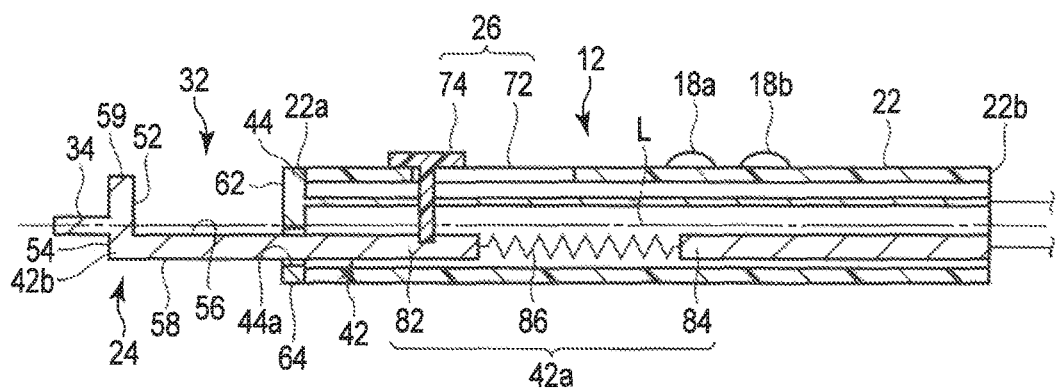
FIG. 8A is a schematic diagram illustrating a treatment instrument of a treatment system according to a fifth embodiment, and illustrating a state in which a first treatment section of a treatment area is switched to an opened position.
Figure 8B:
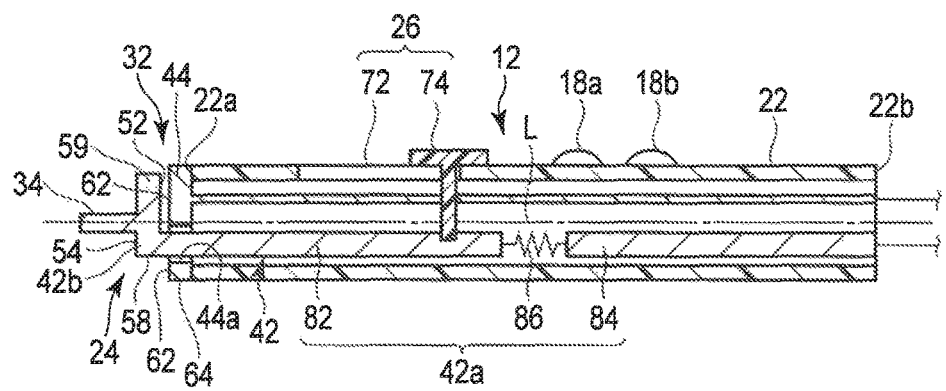
FIG. 8B is a schematic diagram illustrating the treatment instrument of the treatment system according to the fifth embodiment, and illustrating a state in which the first treatment section of the treatment area is switched to a closed position.

The following is explanation of a fifth embodiment, with reference to FIG. 8A and FIG. 8B. The present embodiment is a modification of the fourth embodiment. The same members or members having the same functions as the members explained in the fourth embodiment are denoted by the same reference numerals as much as possible, and detailed explanation thereof is omitted.

As illustrated in FIG. 8A and FIG. 8B, the distal end of the second body 44 is provided with a through hole 44a formed in parallel with the longitudinal axis L. An internal circumferential surface of the through hole 44a is electrically insulated.

The shaft 42a of the first body 42 includes a distal side member 82, a proximal side member 84, and an energizing body 86. The proximal side member 84 is fixed with respect to the sheath 22. The distal side member 82 is coupled with the proximal side member 84 through the energizing body 86. A proper spring such as a helical extension spring is used as the energizing member 86. The energizing body 86 energizes a proximal end 82a of the distal side member 82 toward a distal end 84a of the proximal side member 84. The energizing body 86 may have electrical conductivity to electrically connect the proximal side member 84 with the distal side member 82. As another example, the energizing body 86 having electrical insulation property may be used, when the proximal side member 84 is electrically connected with the distal side member 82 with a lead (not illustrated).

The distal side member 82 is disposed in a state of running through the through hole 44a of the second body 44. The slide lever 74 having electrical insulation property is fixed to the distal side member 82. The slide lever 74 is movable within a predetermined range with the groove 72.

As illustrated in FIG. 8A, when the slide lever 74 is moved toward the distal side along the groove 72 against the energizing force of the energizing body 86, the first contact surface 52 of the distal side member 82 is disposed distant from the second contact surface 62 of the second body 44, and the first treatment section is changed to the opened position.

As illustrated in FIG. 8B, when the slide lever 74 is disposed at the proximal end of the groove 72 by the energizing force of the energizing body 86, the first contact surface 52 of the distal side member 82 is disposed close to the second contact surface 62 of the second body 44, and the first treatment section is changed to the closed position.

In this state, the first switch 18a and the second switch 18b are properly operated, to perform proper treatment.

The treatment instrument 12 according to the present embodiment can be used in the same manner as the treatment instrument 12 explained in the first embodiment, and explanation of functions thereof is omitted.

The treatment instrument 12 according to the present embodiment enables application of pressure to the living tissue with the energizing body 86, in the state where the living tissue such as a blood vessel is disposed between the first contact surface 52 and the second contact surface 62. In this state, the user's operation of pressing the slide lever 74 can be omitted, according to the type of the living tissue. In addition, the energizing force of the energizing member 86 enables uniform treatment, such as coagulation and sealing, for the living tissue.

Figure 9:
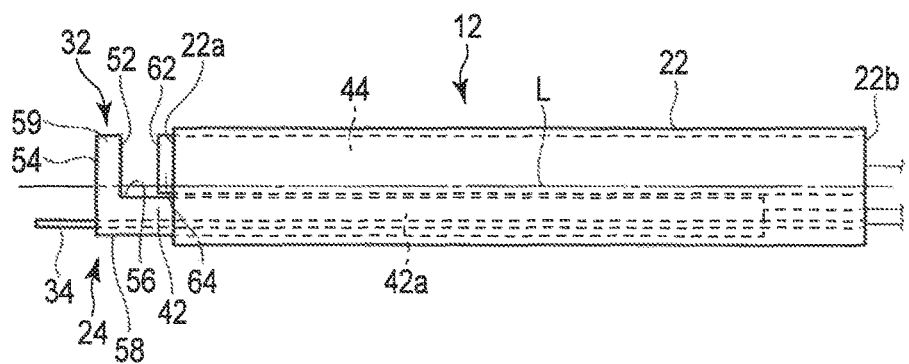
FIG. 9 is a schematic diagram illustrating a treatment instrument of a treatment system according to a sixth embodiment.
Figure 10A:
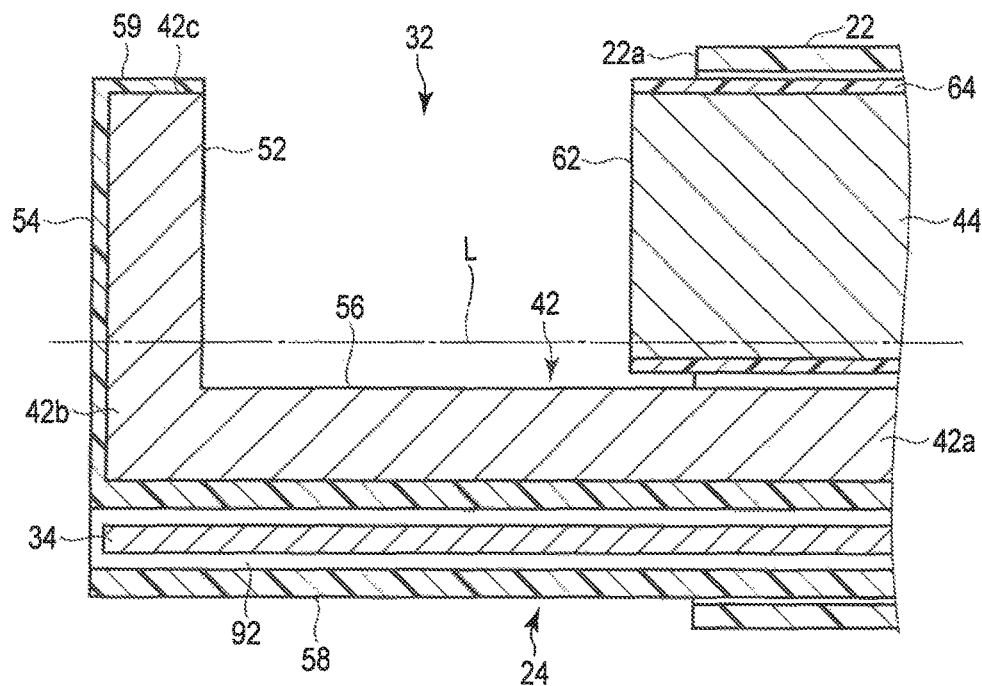
FIG. 10A is a schematic diagram illustrating a treatment area of the treatment instrument of the treatment system according to the sixth embodiment in an enlarged state, and illustrating a state in which the first treatment section of the treatment area is switched to an opened position.
Figure 10B:
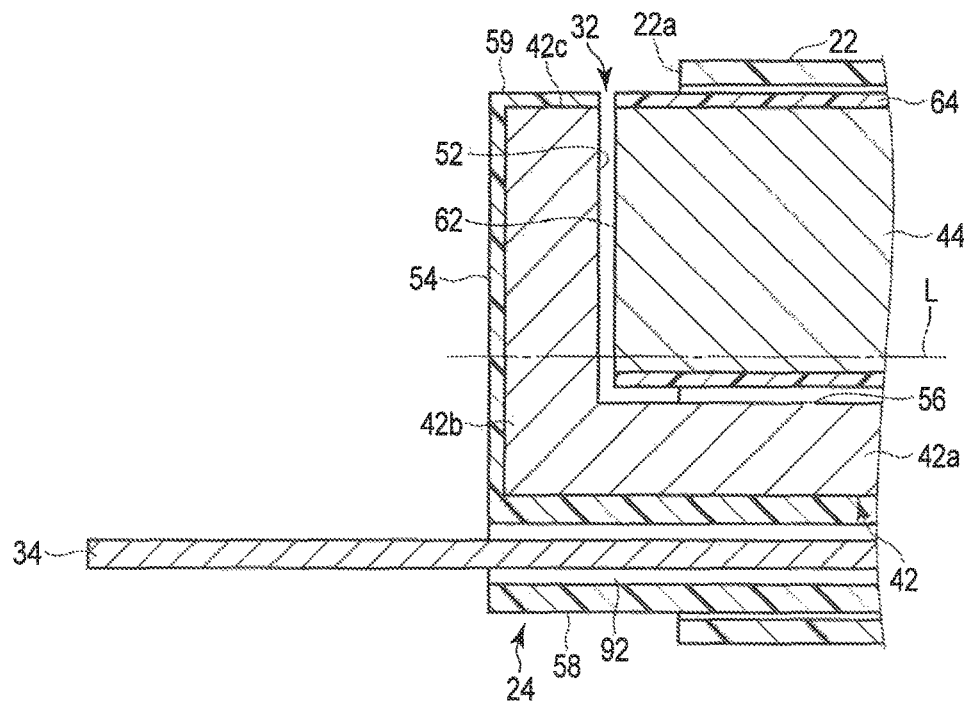
FIG. 10B is a schematic diagram illustrating the treatment area of the treatment instrument of the treatment system according to the sixth embodiment in an enlarged state, and illustrating a state in which the first treatment section of the treatment area is switched to a closed position.

The following is explanation of a sixth embodiment, with reference to FIG. 9 to FIG. 10B. The present embodiment is a modification of the first to the fifth embodiments. The same members or members having the same functions as the members explained in the first to the fifth embodiments are denoted by the same reference numerals as much as possible, and detailed explanation thereof is omitted.

As illustrated in FIG. 9 to FIG. 10B, in the present embodiment, the second treatment section 34 is formed as a member separated from the first body 42 of the first treatment section 32, not as a united member. For this reason, the second treatment section 34 is not required to have the same potential as that of the first body 42 of the first treatment section 32.

As illustrated in FIG. 10A and FIG. 10B, the first body 42 of the first treatment section 32 includes a channel 92 formed in parallel with the longitudinal axis L and including an insulated internal circumferential surface. In this example, the channel 92 is formed on the back surface side with respect to the region denoted by reference numeral 56. The second treatment section 34 in a rod shape is disposed in the channel 92. The second treatment section 34 is fixed with respect to the sheath 22.

As illustrated in FIG. 10A, when the first contact surface 52 and the second contact surface 62 are switched to the opened position, the second treatment section 34 is covered with the channel 92. As illustrated in FIG. 10B, when the first contact surface 52 and the second contact surface 62 are switched to the closed position, the second treatment section 34 projects from the channel 92.

For this reason, when the user uses the treatment instrument 12 to perform treatment, the user switches the first treatment section 32 to the closed position, to cause the second treatment section 34 to project from the first treatment section 32 toward the distal end side. In this state, for example, the second switch 16b of the foot switch 16 is pressed, to perform monopolar-type treatment on the living tissue with the second treatment section 34 of the treatment area 24. Monopolar-type high-frequency energy is applied to the living tissue serving as treatment target, and the high-frequency energy is recovered with the patient plate P attached to the patient, to incise the living tissue caused to contact the second treatment section 34, or separate layers of the living tissue.

When the electrical insulation sections 54, 58, and 59 of the first treatment section 32 contact the living tissue in a proper position, no electricity flows through the contacting living tissue. With the structure, the electrical insulation sections 54, 58, and 59 of the first treatment section 32 prevent a high-frequency current from unintentionally flowing through the living tissue. Specifically, this structure prevents unintentional treatment with the treatment area 24.

For example, when a blood vessel is exposed, the user switches the first treatment section 32 to the opened position, to retract the second treatment section 34 into the channel 92 with respect to the first treatment section 32. In this state, the blood vessel is disposed between the first contact surface 52 of the first body 42 of the first treatment section 32 and the second contact surface 62 of the second treatment section 34. The user switches the first treatment section 32 to the closed position, to bring the blood vessel into contact with both the first contact surface 52 of the first body 42 and the second contact surface 62 of the second treatment section 34. In this state, the first switch 16a is pressed, to perform bipolar-type treatment on the living tissue serving as treatment target, such as a blood vessel, with the first treatment section 32, and seal the blood vessel.

As explained in the fifth embodiment, the shaft 42a of the first body 42 illustrated in FIG. 9 to FIG. 10B may be provided to be movable along the longitudinal axis L, in the through hole 44a of the second body 44.

Figure 11C:
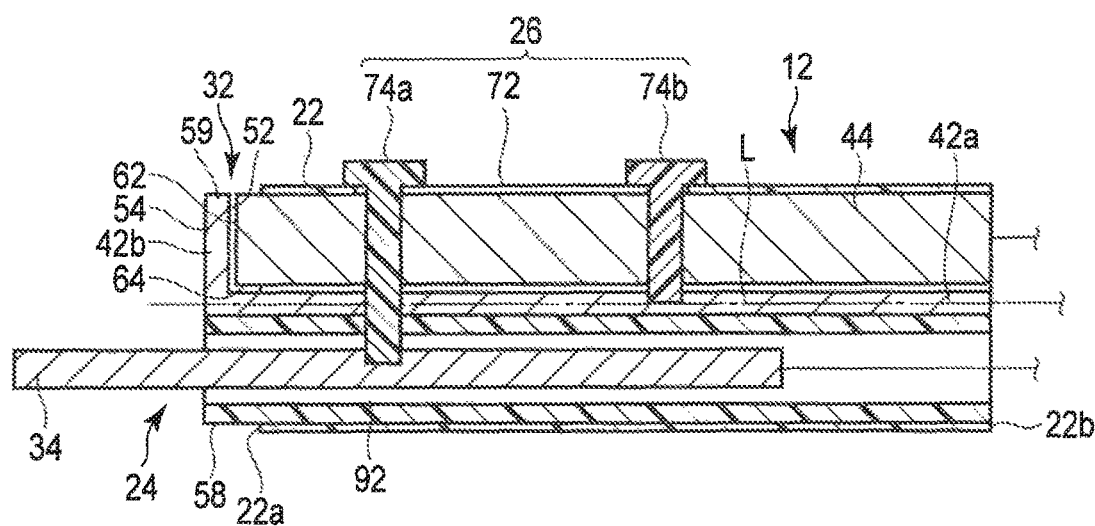
FIG. 11C is a schematic diagram illustrating a state in which the movement mechanism of the treatment instrument of the treatment system according to the seventh embodiment is operated to switch the first treatment section of the treatment area is switched to the closed position, and the second treatment section is caused to project from a distal end of the first treatment section.

The following is explanation of a seventh embodiment, with reference to FIG. 11A to FIG. 11C. The present embodiment is a modification of the first to the sixth embodiments. The same members or members having the same functions as the members explained in the first to the sixth embodiments are denoted by the same reference numerals as much as possible, and detailed explanation thereof is omitted. In particular, the present embodiment is a modification of the sixth embodiment.

As illustrated in FIG. 11A to FIG. 11C, the movement mechanism 26 includes the groove 72, a first slide lever 74a, and a second slide lever 74b. The groove 72 is shared between the first slide lever 74a and the second slide lever 74b. The first slide lever 74a is disposed on the distal side in the groove 72 along the longitudinal axis L, with respect to the second slide lever 74b. The first slide lever 74a is coupled with the second treatment section 34. The second slide lever 74b is coupled with the shaft 42a of the first body 42 of the first treatment section 32.

When no treatment is performed, as illustrated in FIG. 11A, the first slide lever 74a and the second slide lever 74b are positioned on the most proximal side with respect to the groove 72. Specifically, the first treatment section 32 is switched to the closed position, and the second treatment section 34 is disposed on the proximal side with respect to the distal end of the action section 42b of the first body 42 of the first treatment section 32.

When a blood vessel or the like is sealed with the first treatment section 32, as illustrated in FIG. 11B, the first slide lever 74a and the second slide lever 74b are positioned on the most distal side with respect to the groove 72. Specifically, the first treatment section 32 is switched to the opened position, and the second treatment section 34 is disposed on the proximal side with respect to the distal end of the action section 42b of the first body 42 of the first treatment section 32.

When a thin membrane is incised or the living tissue is separated with the second treatment section 32, as illustrated in FIG. 11C, the first slide lever 74a is positioned on the most distal side with respect to the groove 72, and the second slide lever 74b is positioned on the most proximal side with respect to the groove 72. Specifically, the first treatment section 32 is switched to the closed position, and the second treatment section 34 is caused to project with respect to the distal end of the action section 42b of the first body 42 of the first treatment section 32. With the structure, the second treatment section 34 is enabled to project to the distal side along the longitudinal axis with respect to the first body 42 of the first treatment section 32.

When the user uses the treatment instrument 12 to perform treatment and dispose the treatment area 24 in a proper position, the user moves the first and the second slide levers 74a and 74b of the movement mechanism 26 to the state illustrated in FIG. 11A, or the state illustrated in FIG. 11C.

Thereafter, the first and the second slide levers 74a and 74b are moved to the state illustrated in FIG. 11A or FIG. 11C, to cause the second treatment section 34 to project with respect to the distal end of the action section 42b of the first body 42 of the first treatment section 32. In this state, for example, the second switch 16b of the foot switch 16 is pressed, to perform monopolar-type treatment on the living tissue with the second treatment section 34 of the treatment area 24. This structure causes the second treatment section 34 to incise the contacting living tissue such as a thin membrane, or separate layers of the living tissue.

For example, when a blood vessel is exposed, the user moves the first and the second slide levers 74a and 74b to the state illustrated in FIG. 11B, to switch the first treatment section 32 to the opened section, and retract the second treatment section 34 into the channel 92 with respect to the first treatment section 32. In this state, the blood vessel is disposed between the first contact surface 52 of the first body 42 of the first treatment section 32 and the second contact surface 62 of the second treatment section 34. The user moves the first and the second slide levers 74a and 74b to the state illustrated in FIG. 11C, to switch the first treatment section 32 to the closed position, and cause the blood vessel to contact both the first contact surface 52 of the first body 42 and the second contact surface 62 of the second treatment section 34. In this state, the first switch 16a is pressed, to perform bipolar-type treatment on the living tissue serving as treatment target, such as a blood vessel, with the first treatment section 32, and seal the blood vessel.

As described above, for example, when treatment is performed with the first treatment section 32, the second treatment section 34 can be contained in the first treatment section 32, as illustrated in FIG. 11A and FIG. 11B. This structure prevents the second treatment section 34 from becoming an obstacle.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
a sheath that defines a longitudinal axis by a distal end and a proximal end;
a first treatment section that includes:
a first body including a first contact surface having conductivity, the first body crossing the longitudinal axis and being configured to contact a living tissue, and the first body having a first electrical insulation section having electrical insulation properties, and
a second body including a second contact surface opposed to the first contact surface on a proximal side with respect to the first contact surface and configured to contact the living tissue,
the first treatment section being configured to apply energy to the living tissue held between the first contact surface and the second contact surface to coagulate the living tissue;
a movement mechanism that is configured to move at least one of the first body and the second body along the longitudinal axis, to switch between:
a closed position in which the first contact surface and the second contact surface are close to each other, and
an opened position in which the first contact surface and the second contact surface are distant from each other; and
a second treatment section that has conductivity, the second treatment section projecting from a back surface of the first contact surface of the first body and extending along the longitudinal axis, and the second treatment section being configured to apply energy to the living tissue to incise or separate the living tissue,
wherein the first electrical insulation section is provided between the first contact surface and the second treatment section.

2. The treatment instrument according to claim 1, wherein:
the second treatment section is configured to perform monopolar-type treatment on the living tissue.

3. The treatment instrument according to claim 1, wherein:
the first contact surface and the second contact surface are configured to flow high-frequency energy to the first contact surface and the second contact surface and are configured to coagulate the living tissue with bipolar treatment on the living tissue held between the first contact surface and the second contact surface, and
the second treatment section is configured to incise or separate the living tissue with monopolar-type treatment on the living tissue.

4. The treatment instrument according to claim 1, wherein the first contact surface of the first treatment section and the second treatment section have an equal electric potential.

5. The treatment instrument according to claim 1, wherein the second treatment section is formed as one unitary piece with the first body of the first treatment section.

6. The treatment instrument according to claim 1, wherein at least one of the first contact surface and the second contact surface includes a heater configured to apply thermal energy to the living tissue.

7. The treatment instrument according to claim 1, further comprising an energizing body that is configured to perform energization in a direction of causing the first body and the second body to become close to each other.

8. The treatment instrument according to claim 1, wherein at least one of the first contact surface and the second contact surface is inclined in a state between a state parallel with the longitudinal axis and a state orthogonal to the longitudinal axis.

9. The treatment instrument according to claim 1, wherein the first contact surface and the second contact surface are parallel with each other.

10. The treatment instrument according to claim 1, wherein the first electrical insulation section is provided between the first contact surface and a distal end of the second treatment section along the longitudinal axis.

11. The treatment instrument according to claim 1, wherein the first electrical insulation section is formed on the back surface with respect to the first contact surface.

12. The treatment instrument according to claim 1, wherein the second body includes an electrical insulation section having electrical insulation properties and that is provided on an external circumferential surface of the second body.

13. The treatment instrument according to claim 1, wherein the first treatment section includes a second electrical insulation section having electrical insulation properties, the second electrical insulation section being continuous with the first electrical insulation section and being provided on an external circumferential surface of the first body around the longitudinal axis.

14. The treatment instrument according to claim 1, wherein the first body includes a projection having electrical insulation properties and that is disposed on the first contact surface.

15. The treatment instrument according to claim 14, wherein:
the first body includes:
  a shaft extending in parallel with the longitudinal axis;
  an action section formed by bending a distal end of the shaft in a direction crossing the longitudinal axis; and
  a far end with respect to the shaft; and
the projection is disposed in the vicinity of the far end with respect to the shaft.

16. The treatment instrument according to claim 15, wherein:
the first contact surface and the second contact surface are inclined in a state between a state parallel with the longitudinal axis and a state orthogonal to the longitudinal axis,
a first normal of the first contact surface of the first body is directed towards the proximal side along the longitudinal axis, and towards a side opposite to the shaft of the first body, and
a second normal of the second contact surface of the second body is directed towards a distal side along the longitudinal axis, and towards the shaft or the action section of the first body.

17. The treatment instrument according to claim 1, wherein the second treatment section is disposed on a distal side with respect to the first treatment section along the longitudinal axis.

* * * * *